US012154666B2

(12) United States Patent
Kruger et al.

(10) Patent No.: US 12,154,666 B2
(45) Date of Patent: Nov. 26, 2024

(54) SYSTEM AND METHODS FOR CREATING NON-FUNGIBLE TOKENS

(71) Applicant: NFTME, LLC, Milwaukee, WI (US)

(72) Inventors: Bradley Kruger, Milwaukee, WI (US); Laura Spurr, Milwaukee, WI (US)

(73) Assignee: NFTME, LLC, Milwaukee, WI (US)

( * ) Notice: Subject to any disclaimer, the term of this patent is extended or adjusted under 35 U.S.C. 154(b) by 71 days.

(21) Appl. No.: 17/677,601

(22) Filed: Feb. 22, 2022

(65) Prior Publication Data

US 2022/0406419 A1     Dec. 22, 2022

Related U.S. Application Data

(60) Provisional application No. 63/211,148, filed on Jun. 16, 2021.

(51) Int. Cl.
| | |
|---|---|
| *G16H 10/60* | (2018.01) |
| *G06Q 20/36* | (2012.01) |
| *G16H 15/00* | (2018.01) |
| *H04L 9/00* | (2022.01) |

(52) U.S. Cl.
CPC .......... *G16H 10/60* (2018.01); *G06Q 20/363* (2013.01); *G06Q 20/3674* (2013.01); *G16H 15/00* (2018.01); *H04L 9/50* (2022.05)

(58) Field of Classification Search
CPC .......... G16H 15/00; G16H 10/60; H04L 9/50; G06Q 20/363; G06Q 20/3674

USPC .......................................................... 705/2
See application file for complete search history.

(56) References Cited

U.S. PATENT DOCUMENTS

| | | |
|---|---|---|
| 10,505,726 B1* | 12/2019 | Andon et al. |
| 2022/0006642 A1* | 1/2022 | Maj et al. |
| 2022/0084665 A1* | 3/2022 | Blackburn et al. |
| 2022/0246299 A1* | 8/2022 | Gilvert |
| 2022/0318233 A1* | 10/2022 | Martinz |
| 2023/0119641 A1* | 4/2023 | Meyers et al. |

FOREIGN PATENT DOCUMENTS

CN      110600096 A  *  12/2019

* cited by examiner

*Primary Examiner* — Neha Patel
*Assistant Examiner* — Yin Y Choi
(74) *Attorney, Agent, or Firm* — Scherrer Patent & Trademark Law, P.C.; Stephen T. Scherrer; Monique A. Morneault

(57) ABSTRACT

Systems and methods for creating non-fungible tokens ("NFTs"), preferably of medical imagery, automates the creation of NFTs utilizing a software application integrated with an imaging device. In preferred embodiments, the imaging device is a medical imaging device, a device associated with the imaging device, or otherwise resident on a computing device. In other embodiments, the software application is associated with medical record systems. Thus, the software application automatically creates an NFT based on imagery created by the imaging device and incorporates associated image, owner and/or software identifiers.

16 Claims, 2 Drawing Sheets

SYSTEM AND METHODS FOR CREATING NON-FUNGIBLE TOKENS

The present invention claims priority to U.S. Prov. Pat. App. No. 63/211,148, titled "Systems and Methods for Creating Non-Fungible Tokens," filed Jun. 16, 2021, which is incorporated herein by reference in its entirety.

TECHNICAL FIELD

The present invention relates to systems and methods for creating non-fungible tokens ("NFTs"), preferably of medical imagery. Specifically, the present invention automates the creation of NFTs utilizing a software application integrated with an imaging device. In preferred embodiments, the imaging device is a medical imaging device, a device associated with the imaging device, or otherwise resident on a computing device, such as a computer, smart phone, tablet computer, or other like computing device. In other embodiments, the software application is associated with medical record systems. Thus, the software application automatically creates an NFT that is attached to imagery created by the imaging device and incorporates associated image, owner and/or software identifiers.

BACKGROUND

It is, of course, generally known to store videos and pictures of one's internal body through imaging technology. For example, machines may utilize sound waves, X-rays, magnetic fields, and other like technology to image internal structures of someone's body. These images are typically utilized in diagnosing disease and providing health care.

In addition to medical research, many do not realize that internal images of patients are often sold to for-profit companies such as insurance, pharmaceutical, medical device, and other large corporations for business purposes. For example, a patient may be referred by a medical provider to a medical facility to get a medical image, such as, for example, an ultrasound image. The patient typically schedules the ultrasound, arrives at the appointment, which is typically an outpatient clinic, and sits for an ultrasound by a certified ultrasound technician. When the ultrasound is performed, the patient can typically see, in real-time, the imagery (known as "echoes") of their internal body. This imagery is typically recorded and transformed into video, audio and/or photographic images for the physician to review for diagnostic purposes. Typically, the ultrasound video, audio and/or images are kept within the medical facility's medical record system. Under current law, a patient can request copies of the imagery, though often the patient does not receive the imagery voluntarily by the medical facility.

The medical facility can commoditize the imagery for their own profit. Typically, the medical facility de-identifies the images utilizing one of two methods to achieve de-identification in accordance with HIPAA and GDPR privacy rules. Once de-identified, the practicing facility can commercialize the imagery by selling the imagery to for-profit corporations, research facilities, laboratories, or other like receivers of the de-identified information. The patient is not typically notified of the commoditization and there is typically little to no value provided to the patient for the commercialization of their internal body. All profits typically go to the medical facility and its organization.

A need, therefore, exists for improved systems and methods for allowing patients to retain the ownership of medical imagery of their own internal bodies. Specifically, a need exists for improved systems and methods that provide patients with the ability to commercialize the medical imagery of their own internal bodies at their own discretion for their gain. More specifically, a need exists for improved systems and methods for allowing patients to limit commercialization of their own medical imagery through retained ownership and tracking. Such an invention has the potential for strong financial benefits to the patients, many of whom currently struggle to pay medical bills while their medical institutions benefit generously from the patient's internal imagery.

Moreover, there are currently no automated mechanisms for tracking medical imagery and retaining associated information concerning the medical imagery. For example, there is no consistent means for tracking which device imagery came from, which can cause financially intensive incidents to patients and medical institutions. Specifically, associated information concerning medical imagery that may be useful includes an identification of the specific medical imaging unit, the specific probe or other medical device or devices attached to the unit, the amount of radiation and/or other pertinent information that is specific to each individual test or scan, including the name of the technician. A need, therefore, exists for improved systems and methods for compiling and tracking pertinent information relating to or otherwise associated with the generation of medical imagery. Specifically, a need exists for improved systems and methods that provides medical device companies, healthcare institutions, and/or patients the ability to have retrospective review of medical imaging devices should issues arise in the future due to machine component failures, device recalls, technician negligence or training issues, and/or other potential safety issues.

Typically, digital files can be copied repeatedly, and ownership of digital files are kept on servers controlled by institutions. Thus, it is often difficult to prove ownership of digital files. Companies that rely on ownership details of digital files, such as digital tickets for events, for example, oftentimes must build their own ticket exchange, where the ownership of the digital ticket remains within their own ticket exchange. Creators of these digital files must typically rely on the infrastructure and platforms that they build and use. Because digital files can be copied, ownership and tracking of these digital files becomes problematic. With respect to medical imagery, once de-identified and/or sold, it is often difficult to provide assurances of ownership and/or accuracy of imagery, typically unless the imagery comes directly from a medical facility. A need, therefore, exists for improved systems and methods for identifying ownership and accuracy of medical imagery. Specifically, a need exists for improved systems and methods for allowing individuals the means to generate value from the commercialization and ongoing profits of their own medical imagery.

Non-fungible tokens ("NFTs") are tokens that have linked digital files ("assets") that, using blockchain technology, provide an owner of the file certification that the digital asset is unique. More specifically, an NFT is a unit of data stored on a digital ledger, called a blockchain, that certifies a digital asset to be unique and therefore not interchangeable. NFTs can be used to represent items such as photos, videos, audio, and other types of digital files. Typically, while access to any copy of the original file may not be typically restricted to the buyer of an NFT, NFTs are tracked on blockchains to provide the owner with a proof of ownership.

Beginning in 2020, there has been increased interest in creating NFTs. Largely due to the rise in interest in the global cryptocurrency market and increasing digital economy, blockchains like Ethereum, Flow, and Tezos have their own standards when it comes to supporting NFTs, but each works to ensure that the digital item represented is authentically one-of-a-kind. NFTs are now being used to commodify digital assets in art, music, sports, and other popular entertainment. Many NFTs are part of the Ethereum blockchain; however, other blockchains are beginning to grow in their adoption of NFTs.

NFTs are oftentimes difficult to create, and typically involve a complex and technical process that the average person may not be able to do without significant cost and additional resources, such as third-party resources. Often, if a user wishes to create an NFT from a digital file, he or she must typically find the right platform for NFT creation, and pay upfront costs to utilize the blockchain to tokenize the digital file.

A wallet, as described herein, must be created that stores the user's private key which is needed to authorize transactions. The wallet acts as a repository for all cryptocurrencies and NFTs and the wallet ID designates ownership.

Next, the Inter-Planetary File System ("IPFS") or comparable cloud storage solution is utilized, wherein the media can be stored to be associated with the NFT. Within the two networks and through the digital wallet interface, the NFT may be created. Often, an NFT "Smart Contract" is created first to create the NFT Tokens (which are the desired NFTs). A parent contract allows for the creation of the NFTs, and the NFT contract's address keeps the NFTs together as a family. Before an NFT, the desired media is uploaded to IPFS or other similar system, thereby obtaining an IPFS URL link. The IPFS URL link is added to the NFT information field, thereby creating the NFT token, which is non-fungible because the token cannot be split into fractions, nor can it have a duplicate.

A need, therefore, exists for improved systems and methods for creating NFTs. More specifically, a need exists for improved systems and methods for allowing individuals to create NFTs of their medical imagery.

SUMMARY OF THE INVENTION

The present invention relates to systems and methods for creating non-fungible tokens ("NFTs"), preferably of medical imagery. Specifically, the present invention automates the creation of NFTs utilizing a software application integrated with an imaging device. In preferred embodiments, the imaging device is a medical imaging device, a device associated with the imaging device, or otherwise resident on a computing device, such as a computer, smart phone, tablet computer, or other like computing device. In other embodiments, the software application is associated with medical record systems. Thus, the software application automatically creates an NFT based on imagery created by the imaging device and incorporates associated image, owner and/or software identifiers.

To this end, in an embodiment of the present invention, a medical device imaging system comprises a software application resident thereon or otherwise associated therewith, the software application utilized in a method to generate an NFT from medical imagery, the method comprising the steps of: generating medical imagery; deploying a master Smart Contract, uploading the media to a storage solution, "minting" the NFT and linking it to the uploaded media, creating the NFT on the blockchain; linking to a user's crypto wallet and delivering the NFT to the user's crypto wallet.

In another embodiment of the present invention, a system for creating and claiming a non-fungible token (NFT) of a user's medical data is provided. The system comprises: a medical device configured to record medical record data of a user, wherein the recorded medical data; and a processor comprising a communication module and a memory controlled by the processor, the memory including instructions that when executed by the processor cause the processor to perform the steps of: receiving the recorded medical data of the user; creating a non-fungible token using the recorded medical data; and transmitting the non-fungible token of the recorded medical data to a secure smart wallet.

In an embodiment, the processor receives the recorded medical data of the user and the additional information via the communication module.

In an embodiment, the recorded medical data of the user further includes additional information.

In an embodiment, the additional information is selected from the group of: a unique identification number, a timestamp, an institution identification, a machine identification, a technician identification, and combinations thereof.

In an embodiment, the recorded medical data is selected from the group of: a video, a still image, an audio file, a graph, a chart, a table, and combinations thereof.

In an embodiment, the medical device is selected from the group of: an electronic medical record system, an electronic health record system, an ultrasound machine, a Doppler ultrasound machine, an echocardiography machine, an MRI machine, a CAT scan machine, an X-ray machine, a computed tomography (CT) machine, a nuclear medical imaging machine, a positron emission tomography (PET) machine, a fluoroscope, a pacemaker, a defibrillator, a brachytherapy apparatus, a myelogram machine, a mammogram machine, and combinations thereof.

In an embodiment, the processor is a component of the medical device.

In an embodiment, the processor is a component of a personal communication device.

In an embodiment, the personal communication device comprises a graphical user interface through which a user of the personal communication device instructs the processor to create the non-fungible token using the user's medical data.

In an embodiment, the graphical user interface allows the user to instruct the processor to claim the non-fungible token using the user's medical data and record the non-fungible token in a smart contract that is stored in the user's secure smart wallet.

In an alternate embodiment of the present invention, a method for creating and claiming a non-fungible token (NFT) of a user's medical data is provided. The method comprises the steps of: providing a medical device configured to record medical data of a user; recording medical data of a user using the medical device; communicating with a processor comprising a communication module and a memory controlled by the processor; and sending the user's recorded medical data to the processor, wherein the user's medical data is converted into a non-fungible token, and the non-fungible token of the user's recorded medical data is transmitted to a secure smart wallet.

In an embodiment, the processor receives the recorded medical data of the user via the communication module.

In an embodiment, the recorded medical data includes additional information, wherein the additional information is selected from the group of: a unique identification number, a timestamp, an institution identification, a machine identification, a technician identification, and combinations thereof.

In an embodiment, the recorded medical data is selected from the group of: a video, a still image, an audio file, a graph, a chart, a table, and combinations thereof.

In an embodiment, the medical device is selected from the group of: an electronic medical record system, an electronic health record system, an ultrasound machine, a Doppler ultrasound machine, an echocardiography machine, an MRI machine, a CAT scan machine, an X-ray machine, a computed tomography (CT) machine, a nuclear medical imaging machine, a positron emission tomography (PET) machine, a fluoroscope, a pacemaker, a defibrillator, a brachytherapy apparatus, a myelogram machine, a mammogram machine, and combinations thereof.

In an embodiment, the processor is a component of the medical device.

In an embodiment, the processor is a component of a personal communication device.

In yet another alternate embodiment of the present invention, a method for creating and claiming a non-fungible token (NFT) of a user's medical data is provided. The method comprises the steps of: providing a processor with a communication module and a memory; receiving, at the processor, recorded medical data of a user from a medical device via the communication module; converting the user's recorded medical data into a non-fungible token; and transmitting the non-fungible token to a secure smart wallet.

In an embodiment, the processor is a component of a personal communication device, wherein the personal communication device comprises a graphical user interface through which a user of the personal communication device instructs the processor to create the non-fungible token using the user's medical data.

In an embodiment, the graphical user interface allows the user to instruct the processor to claim the non-fungible token using the user's medical data and record the non-fungible token in a smart contract that is stored in the user's secure wallet.

It is, therefore, an advantage and objective of the present invention to provide improved systems and methods for allowing patients to retain the ownership of medical imagery of their own internal bodies.

More specifically, it is an advantage and objective of the present invention to provide improved systems and methods for allowing patients to control commercialization of their own medical imagery through retained ownership and tracking. Further, the present invention would enable patients to receive incentive for commercializing their own medical data, therefore balancing the current healthcare cost dilemma which exists in the United States.

In addition, it is an advantage and objective of the present invention to provide improved systems and methods for compiling and tracking pertinent information relating to or otherwise associated with the generation of medical imagery.

Specifically, it is an advantage and objective of the present invention to provide improved systems and methods that provides medical device companies, healthcare institutions, and/or patients the ability to have retrospective review of medical imaging devices should issues arise in the future due to machine component failures, device recalls, technician negligence or training issues, and/or other potential safety issues.

Moreover, it is an advantage and objective of the present invention to provide improved systems and methods for identifying ownership and accuracy of medical imagery.

Further, it is an advantage and objective of the present invention to provide improved systems and methods for creating NFTs.

Still further, it is an advantage and objective of the present invention to provide improved systems and methods for allowing individuals to create NFTs of their medical imagery.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE PRESENTLY PREFERRED EMBODIMENTS

Figure 1:
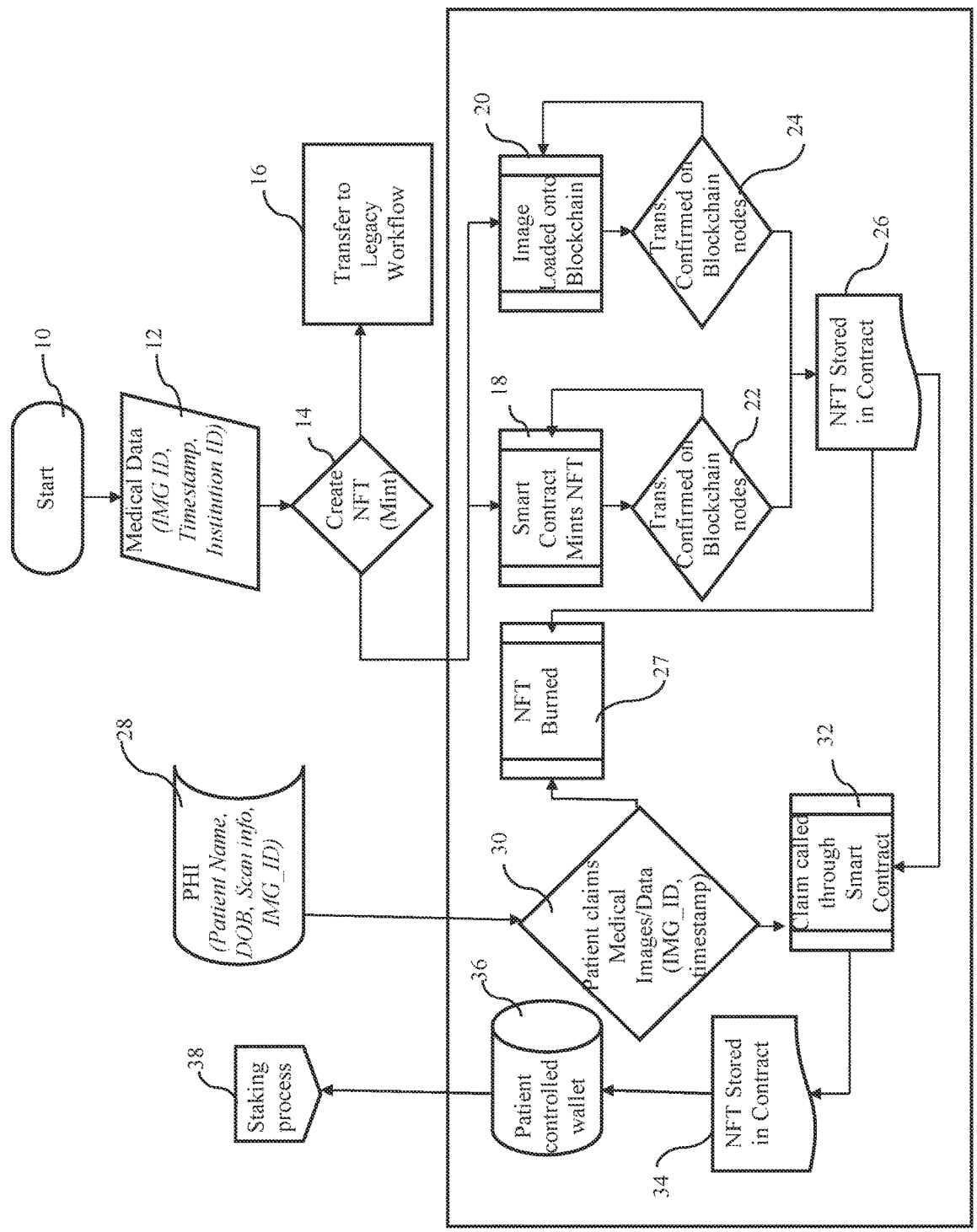
FIG. 1 illustrates a flow chart showing a method of generating NFTs from medical data in an embodiment of the present invention.

The present invention relates to systems and methods for creating non-fungible tokens ("NFTs"), preferably of medical imagery. Specifically, the present invention automates the creation of NFTs utilizing a software application integrated with an imaging device. In preferred embodiments, the imaging device is a medical imaging device, a device associated with the imaging device, or otherwise resident on a computing device. In other embodiments, the software application is associated with medical record systems. Thus, the software application automatically creates an NFT based on imagery created by the imaging device and incorporates associated image, owner and/or software identifiers.

Definitions

Blockchain: A system in which a record of transactions/data are maintained across several computers that are linked in a peer-to-peer network.

Mint: The software function that executes a new record on the blockchain that creates a non-fungible piece of data (a "token" or "NFT") within a blockchain.

Wallet: A unique address within the blockchain, controlled by a user or group of users, that can store tokens and authorize actions and executions of functions within smart contracts.

Burn: Invalidation of data and/or tokens from being used any further on the blockchain.

Claim: A smart contract function to take tokens from the contract and move them to a wallet.

Staking: Depositing a blockchain token in exchange for yield.

In an embodiment of the present invention, the systems and methods of the present invention are accomplished via one or more pieces of hardware and software that coordinate to provide the advantages and objectives disclosed herein. In a preferred embodiment, the software may be in the form of an application that is generally associated with a medical imaging device, such as electronic medical record system, an electronic health record system, a standard ultrasound machine, a Doppler ultrasound machine, an echocardiography machine, an MIll machine or CAT scan machine, an X-ray machine, a computed tomography (CT) machine, a nuclear medical imaging machine, a positron emission tomography (PET) machine, a fluoroscope, a pacemaker, a defibrillator, a brachytherapy apparatus, a myelogram machine, a mammogram machine, or any other like apparatus or medical imaging devices that may be used to create and/or store internal imagery of a body, wherein the imagery may be in the form of video, still images, audio, or any other like imagery. In a preferred embodiment, the software application may be resident on medical imaging devices or medical record systems and may be utilized to create an NFT from the medical imagery created thereby. Thus, when a medical imaging device is used to create the medical imagery in the form of a digital file, the software application may automatically generate the NFT, as disclosed in more detail below.

Alternatively, the software application may be resident on a computing device separate from the medical imaging device or medical records system (such as on a separate server, the Cloud, or other like device) but having access to the medical imagery, such that the computing device, via the software application, may communicate with the medical imaging device or medical records system and automatically generate an NFT from the medical imagery generated by the medical imaging device. Therefore, the software application may obtain the medical imagery in the form of a digital file and create the NFT automatically upon receipt of the digital file. For example, the software application may be an application for download onto a smart device, such as a smart phone, tablet computer, laptop computer, desktop computer, wearable computing devices, such as a smart watch or the like, or any other like computing device apparent to one of ordinary skill in the art.

It should be noted that the software application as described herein may be resident on or otherwise connected to, in communication with, or otherwise associated with any imaging device that creates or generates imagery, such that the software application may automatically create an NFT therefrom, as detailed below. For example, the present invention may be resident on, connected to, in communication with or otherwise associated with a personal computing device, such as a smart phone or tablet computer, and may automatically generate an NFT from a digital file created by or otherwise generated from the personal computing device. For example, the software application as described herein may automatically create an NFT from imagery created by the personal computing device. Moreover, the present invention may further provide automatic creation of any kind of digital asset utilizing blockchain technology. The present invention should not be limited as described herein.

In a preferred embodiment of the present invention, the software application automatically compiles pertinent information relating to medical imagery and generates an NFT from the NFT, including the compiled pertinent information. In a first step of the present invention, the software application, as described above, may link to a user's cryptocurrency wallet. Once linked, the software application may remain linked so as not to prompt a user again, or for security may continuously prompt identity of the user each time the software application is used for security purposes. In a second step, the software application may provide options for which blockchain to create the NFT.

The software application may, in a third step, compile data from various sources for association with the digital file. For example, the software may compile information such as medical information that may include the medical provider's name, the imaging technician, the medical device manufacturer, the medical device manufacturing number, the date of the medical image, the time of the medical image, the medical record system. Moreover, other information relating to the patient or user, such as identifying information including the patient's name, birthdate, or any other like information. Further, information concerning the software utilized to generate the NFT may be compiled, such as the identity of the software used to generate the NFT, the manufacturer of the software, the software version, and/or any other like information relating to the software, the blockchain format, or the smart contract code.

In a next step, the software application may digitize the compiled information and automatically add the digitized information to the digital file. Using the smart contract, the software application may then create the digital file on the blockchain, thereby creating the NFT of the combined medical imagery and the compiled information. The digital file, having the combined medical imagery and the compiled information may then be sent or otherwise provided to the user or patient thereof, and the software application may, in a final step, settle all mining fees generated by creating the NFT as described above.

Figure 2:
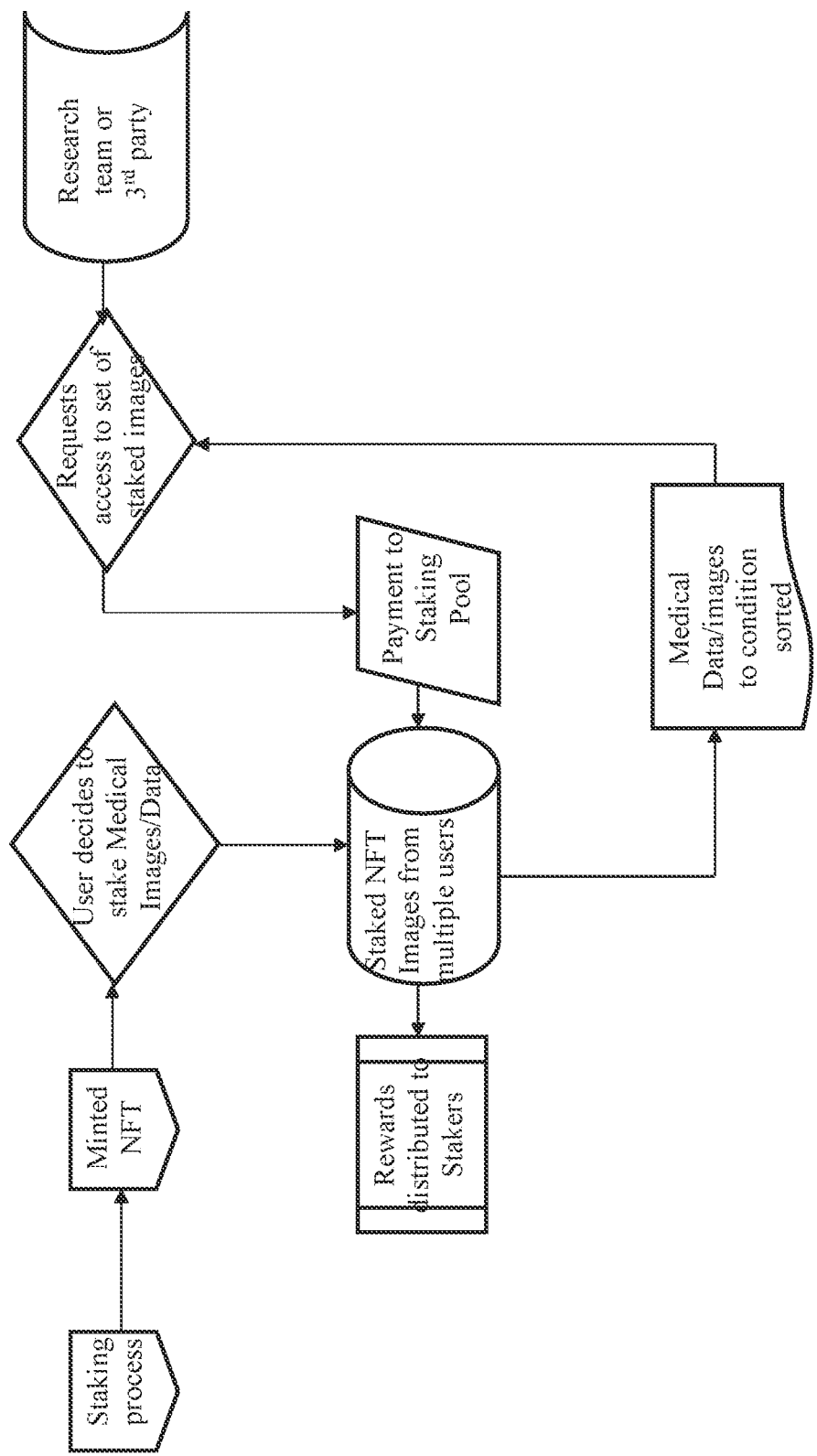
FIG. 2 illustrates a continuing flow chart showing a method of staking NFTs generated from medical data in an embodiment of the present invention.

FIGS. 1 and 2 illustrate an exemplary methodology associated with the present invention. Specifically, the methodology may start at step 10, wherein user medical data in a form disclosed above may be generated via step 12. The user medical data 12 may include the medical data itself and may further have other data associated therewith, such as a unique identification, a timestamp, institution identification, machine identification, technician identification, and other like information. At the creation of the user medical data, the user may be presented with an option to claim the medical data and associated information and convert the same into an NFT via step 14. Thus, the option to claim and create an NFT may be presented to the user via the user's communication device, such as the user's smartphone, and the user may opt to claim and create the NFT by responding affirmatively on the user's communication device, where the medical data and associated information is subsequently automatically converted into an NFT. If a user responds negatively to the option to claim and create the NFT, then the medical data and/or associated data may be transferred to legacy workflow, step 16. Legacy workflow may include the methods of handling user medical data done prior to the present invention.

In an embodiment, creation of the NFT may be done via an application directly associated and/or resident on the medical device that may have created the medical data or within a system tied directly to the medical device. As such, the medical data and associated information may be transferred to an application for processing into an NFT. Alternatively, once the option to claim and create an NFT is affirmatively selected by the user on his or her communication device, the medical data and associated information may be transferred directly to the user's communication device or other system directly controlled by the user. The medical data and associated information may then be converted into an NFT.

In either case, once the user opts to claim and create an NFT from the medical data and the associated information, the medical data and associated information may be minted into an NFT via a Smart Contract, which is a collection of functions/code that may be executed to perform automatic functions related to certain types or subsets of tokens. At the same time, the medical data and associated information may be loaded onto a blockchain via step 20. At the minting of the NFT, the transaction may be confirmed on blockchain nodes via step 22, and if not the process for minting the NFT via the Smart Contract may be repeated. Likewise, after loading the image onto the blockchain via step 20, the transaction may be confirmed on blockchain nodes via step 24, and if not the process for loading the image on the blockchain may be repeated. Once the minting and loading of the NFT is confirmed, the NFT created thereby may be stored in the Smart Contract via step 26. Unclaimed NFTs may be pruned and burned via step 27.

Subsequent to the creation of the NFT after opting to do so by the user, the user may utilize his or her unique information to claim the NFT via steps 28, 30, 32. Step 28 involves utilizing user unique user information and opting to claim the NFT via step 30. The option to claim the NFT may be made by the user via his or her communication device or other application. Thus, upon creation of the NFT, the NFT and associated Smart Contract may be presented to the user for claiming the same via step 30 and, therefore, claimed via step 32. Again, unclaimed medical imagery may cause the NFT associated therewith to be burned via step 27.

Once claimed, the user identification information may be incorporated and stored in the Smart Contract with the NFT via step 34 and subsequently transferred to the user-controlled wallet via step 36, whereupon fees may be settled with respect to the creation and claiming of the NFT by the user. Once stored in a user's wallet via step 36, the user may stake the NFT and derive yield therefrom via step 38.

The staking process (step 38 in FIG. 1) is further shown in detail in FIG. 2, whereupon a user may decide to exchange the NFT for yield. The minted NFT 40 (i.e., the created and claimed NFT stored within the user's smart wallet) may opt to stake the minted NFT 40 via step 42, whereupon the NFT may be stored within a database (called a "staking pool") via step 44 that may be accessible by a research team or third-party team 46. As such, the research or third party team 46 may request access to the database of stored and staked NFTs containing the user's medical data via step 48. The research or third-party team 46 may transfer payment to the staking pool via step 50. Typically, a research or third-party team 46 may be in search of medical data relating to specific conditions. The staking pool may compile the medical data and provide searchable or retrievable NFTs relating to the condition sought. Upon finding medical data in the form of the user's NFT in the staking pool related to the condition sought by the research or third-party team 46, the medical data and associated information of the user's NFT may be transferred to the research or third-party team 46 via step 52. Rewards in the form of payment of yield to the user may then be transferred to the user and retained in the user's smart wallet via step 54.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

We claim:

1. A system for creating and claiming a non-fungible token (NFT) of a patient's medical data, the system comprising:

a medical device configured to create medical data in the form of internal imagery of a first patient's body wherein the internal imagery is selected from the group of a still image, audio, video, and combinations thereof, and record the medical data;

a secure cryptocurrency wallet comprising a private key of the first patient, wherein the secure cryptocurrency wallet comprises a unique address within a first blockchain and further wherein the secure cryptocurrency wallet records and stores NFTs and one or more smart contracts associated with the NFTs and wherein the first patient's private key is used to authorize transactions of the stored NFTs via the one or more smart contracts; and a processor comprising a communication module and a memory controlled by the processor, the memory including instructions that when executed by the processor cause the processor to perform the steps of:

opening a communication with the secure cryptocurrency wallet of the first patient;

receiving the recorded medical data of the first patient's body;

compiling additional information with the medical data of the first patient forming compiled information, wherein the compiled information comprises first medical condition data of the first patient, wherein the first patient has a first medical condition and the first medical condition data relates to the first medical condition;

digitizing the compiled information and forming a digital medical asset with the compiled information;

uploading and storing the digital medical asset within a cloud storage system, wherein the uploaded and stored digital medical asset comprises a URL address within the cloud storage system;

generating a smart contract comprising the digital medical asset, wherein the smart contract comprises first patient ownership data of the digital medical asset;

minting an NFT comprising the URL address of the digital medical asset on the cloud storage system via the smart contract by loading the digital medical asset and the URL address of the digital medical asset onto the first or a second blockchain forming a transaction and generating a public key and a private key for the NFT, wherein the transaction is authorized by the first patient's private key;

confirming the transaction on a blockchain node of the first or the second blockchain;

recording the NFT of the digital medical asset and storing the smart contract within the secure cryptocurrency wallet of the first patient based on the first patient ownership data in the smart contract;

staking the NFT of the digital medical asset into a staking pool thereby locking the NFT in the staking pool to receive yield thereby if selected by a user, wherein authorization to stake the NFT is provided by the first patient using the first patient's private key;

staking at least one other NFT into the staking pool thereby locking the at least one other NFT in the staking pool to receive yield thereby if selected by the user, wherein the at least one other NFT comprises second medical condition data of a second patient, wherein the second medical condition data of the second patient relates to the first medical condition;

sorting the NFT and the at least one other NFT by the first medical condition and grouping the NFT and the at least one other NFT within the staking pool based on the first medical condition prior to offering the staking pool to users for selection of the staking pool and payment thereof;

labelling the staking pool with the first medical condition;

presenting to a user via a graphic user interface an option to select and claim the staking pool labelled with the first medical condition;

transferring the first and second medical condition data of the NFT and the at least one other NFT in the staking pool labeled with the medical condition to the user when the staking pool is selected and claimed by the user and upon payment by the user to the staking pool; and transferring yield to the secure cryptocurrency wallet of the first patient and to a secure cryptocurrency wallet of the second patient based on the payment by the user to the staking pool when the first and second medical condition data of the first medical condition is transferred to the user.

2. The system of claim 1 wherein the processor receives the recorded medical data of the patient and the additional information via the communication module.

3. The system of claim 1 wherein the additional information is selected from the group of: a unique identification number relating to the patient, a timestamp, an institution identification, a machine identification, a technician identification, a doctor's review of the medical data, and combinations thereof.

4. The system of claim 1 wherein the medical device is selected from the group of: an electronic medical record system, an electronic health record system, an ultrasound machine, a Doppler ultrasound machine, an echocardiography machine, an MRI machine, a CAT scan machine, an X-ray machine, a computed tomography (CT) machine, a nuclear medical imaging machine, a positron emission tomography (PET) machine, a fluoroscope, a pacemaker, a defibrillator, a brachytherapy apparatus, a myelogram machine, a mammogram machine, and combinations thereof.

5. The system of claim 1 wherein the processor is a component of the medical device.

6. The system of claim 1 wherein the processor is a component of a personal communication device.

7. The system of claim 6 wherein the personal communication device comprises a graphical user interface through which a user of the personal communication device instructs the processor to create the non-fungible token using the patient's medical data.

8. The system of claim 7 wherein the graphical user interface allows the user to instruct the processor to claim the non-fungible token.

9. A method for creating and claiming a non-fungible token (NFT) of a patient's medical data, the method comprising the steps of:

providing a medical device;

creating, by the medical device, medical data in the form of internal imagery of a first patient's body wherein the internal imagery is selected from the group of a still image, audio, video, and combinations thereof;

recording the medical data;

communicating with a processor comprising a communication module and a memory controlled by the processor;

sending the recorded medical data to the processor;

providing a secure cryptocurrency wallet comprising a private key of the first patient, wherein the secure cryptocurrency wallet comprises a unique address within a first blockchain and further wherein the secure cryptocurrency wallet records and stores NFTs and wherein the first patient's private key is used to authorize transactions of the stored NFTs via one or more smart contracts;

opening a communication using the communication module of the processor with the secure cryptocurrency wallet of the first patient;

compiling additional information with the medical data of the first patient forming compiled information, wherein the compiled information comprises first medical condition data of the first patient, wherein the first patient has a first medical condition and the first medical condition data relates to the first medical condition;

digitizing the compiled information and forming a digital medical asset with the compiled information;

uploading and storing the digital medical asset within a cloud storage system, wherein the uploaded and stored digital medical asset comprises a URL address within the cloud storage system;

generating a smart contract comprising the digital medical asset, wherein the smart contract comprises first patient ownership data of the digital medical asset;

minting anon-fungible token an NFT comprising the URL address of the digital medical asset on the cloud storage system via the smart contract by loading the digital medical asset and the URL address of the digital medical asset on the cloud storage system onto the first or a second blockchain forming a transaction for the NFT, wherein the transaction is authorized by the first patient's private key;

confirming the transaction on a blockchain node of the first or the second blockchain;

recording the NFT of the digital medical asset and storing the smart contract within the secure cryptocurrency wallet of the first patient based on the first patient ownership data in the smart contract;

staking the NFT of the digital medical asset into a staking pool thereby locking the NFT in the staking pool to receive yield thereby if selected by a user, wherein authorization to stake the NFT is provided by the first patient's private key;

staking at least one other NFT into the staking pool thereby locking the at least one other NFT in the staking pool to receive yield thereby if selected by the user, wherein the at least one other NFT comprises second medical condition data of another a second patient, wherein the second medical condition data of the second patient relates to the first medical condition;

sorting the NFT and the at least one other NFT by the first medical condition and grouping the NFT and the at least one other NFT within the staking pool based on the first medical condition prior to offering the staking pool to users for selection of the staking pool and payment thereof;

labelling the staking pool with the first medical condition;

presenting to the user via a graphic user interface an option to select and claim the staking pool labelled with the first medical condition;

transferring the first and second medical condition data of the NFT and the at least one other NFT in the staking pool labeled with the medical condition to the user when the staking pool is selected and claimed by the user and upon payment by the user to the staking pool; and transferring yield to the secure cryptocurrency wallet of the first patient and to a secure cryptocurrency wallet of the second patient based on the payment by the user when the first and second medical condition data are transferred to the user.

10. The method of claim 9, wherein the additional information is selected from the group of: a unique identification number of the patient, a timestamp, an institution identification, a machine identification, a technician identification, a doctor's review, and combinations thereof.

11. The method of claim 9 wherein the medical device is selected from the group of: an electronic medical record system, an electronic health record system, an ultrasound machine, a Doppler ultrasound machine, an echocardiography machine, an MRI machine, a CAT scan machine, an X-ray machine, a computed tomography (CT) machine, a nuclear medical imaging machine, a positron emission tomography (PET) machine, a fluoroscope, a pacemaker, a defibrillator, a brachytherapy apparatus, a myelogram machine, a mammogram machine, and combinations thereof.

12. The method of claim 9 wherein the processor is a component of the medical device.

13. The method of claim 9 wherein the processor is a component of a personal communication device.

14. A method for creating and claiming a non-fungible token (NFT) of a patient's medical data, the method comprising the steps of:

providing a secure cryptocurrency wallet comprising a private key of a first owner of the secure cryptocurrency wallet, wherein the secure cryptocurrency wallet comprises a unique address within a first blockchain and further wherein the secure cryptocurrency wallet records and stores NFTs and wherein the first owner's private key is used to authorize transactions of the stored NFTs via one or more smart contracts;

providing a processor with a communication module and a memory; receiving, at the processor, recorded medical data of a first patient wherein the recorded medical data comprises first medical condition data;

opening a communication with the secure cryptocurrency wallet; compiling additional information with the medical data of the first patient forming compiled information, wherein the first medical condition data of the first patient relates to a first medical condition;

digitizing the compiled information and forming a digital medical asset with the compiled information;

uploading and storing the digital medical asset within a cloud storage system, wherein the uploaded and stored digital medical asset comprises a URL address within the cloud storage system;

generating a smart contract comprising the digital medical asset, wherein the smart contract comprises first ownership data of an owner of the digital medical asset;

minting NFT comprising the URL address of the digital medical asset within the cloud storage system via the smart contract by loading the digital medical asset and the URL address of the digital medical asset onto the first or a second blockchain forming a transaction for the NFT, wherein the transaction is authorized by the first patient's private key;

confirming the transaction on a blockchain node of the first or the second blockchain;

recording the private key of the NFT of the digital medical asset and storing the smart contract within the secure cryptocurrency wallet of the first owner based on the first ownership data in the smart contract;

staking the NFT of the digital medical asset into a staking pool thereby locking the NFT in the staking pool to receive yield thereby if selected by a user, wherein authorization to stake the NFT is provided by the first owner's private key;

staking at least one other NFT into the staking pool thereby locking the at least one other NFT in the staking pool to receive yield thereby if selected by the user, wherein the at least one other NFT comprises second medical condition data of a second patient, wherein the second medical condition data of the second patient relates to the medical condition;

sorting the NFT and the at least one other NFT by the first medical condition and grouping the NFT and the at least one other NFT within the staking pool based on the first medical condition prior to offering the staking pool to users for selection of the staking pool and payment thereof;

labelling the staking pool with the first medical condition;

after sorting and grouping the NFT and the one other NFT within the staking pool, and labelling the staking pool with the first medical condition, presenting to a user via a graphic user interface an option to select and claim the staking pool labelled with the first medical condition;

transferring the first and second medical condition data of the NFT and the at least one other NFT in the staking pool labeled with the first medical condition to the user when the staking pool is selected by the user and upon payment by the user to the staking pool; and transferring yield to the secure cryptocurrency wallet of the first owner of the NFT and to a secure cryptocurrency wallet of an owner of the at least one other NFT based on the payment by the user to the staking pool when the first and second medical condition data of the first medical condition are transferred to the user.

15. The method of claim 14 wherein the processor is a component of a personal communication device, wherein the personal communication device comprises a graphical user interface through which a user of the personal communication device instructs the processor to create the NFT.

16. The method of claim 15 wherein the graphical user interface allows the user to instruct the processor to claim the NFT using the user's first medical condition and record the NFT in a smart contract that is stored in the user's a secure smart wallet of the user.

* * * * *